US012763218B2

(12) United States Patent
Cho

(10) Patent No.: US 12,763,218 B2
(45) Date of Patent: Oct. 13, 2026

(54) PET HEALTH MANAGEMENT SERVICE PLATFORM BASED ON ARTIFICIAL INTELLIGENCE LEARNING

(71) Applicant: People In Soft Co., LTD, Sejong-si (KR)

(72) Inventor: Dong Jin Cho, Goyang-si (KR)

(73) Assignee: People In Soft Co., LTD, Sejong-si (KR)

( * ) Notice: Subject to any disclaimer, the term of this patent is extended or adjusted under 35 U.S.C. 154(b) by 0 days.

(21) Appl. No.: 18/754,110

(22) Filed: Jun. 25, 2024

(65) Prior Publication Data

US 2025/0391569 A1 Dec. 25, 2025

(30) Foreign Application Priority Data

Jun. 25, 2024 (KR) ........................ 10-2024-0082362

(51) Int. Cl.

*G16H 50/20* (2018.01)
*G16H 10/60* (2018.01)
*G16H 50/30* (2018.01)

(52) U.S. Cl.

CPC ............. *G16H 50/30* (2018.01); *G16H 10/60* (2018.01); *G16H 50/20* (2018.01)

(58) Field of Classification Search

CPC ......... G16H 50/30; G16H 10/60; G16H 50/20
See application file for complete search history.

(56) References Cited

U.S. PATENT DOCUMENTS

| | | | | |
|---|---|---|---|---|
| 10,943,697 | B2 * | 3/2021 | Boroczky | A61B 5/7267 |
| 2021/0134459 | A1 * | 5/2021 | Crawford | G16H 50/30 |
| 2023/0154623 | A1 * | 5/2023 | Ruple | G06N 20/00 705/2 |
| 2024/0153633 | A1 * | 5/2024 | Palaniappan | G06N 3/088 |
| 2025/0166836 | A1 * | 5/2025 | Foran | G16H 10/20 |

FOREIGN PATENT DOCUMENTS

| | | | |
|---|---|---|---|
| KR | 10-2187344 | B1 | 12/2020 |
| KR | 10-2023-0072540 | A | 5/2023 |

OTHER PUBLICATIONS

Kim Kwang, Song Doo, and Woo Young Machine Intelligence Can Guide Pet Dog Health Pre-Diagnosis for Casual Owner: A Neural Network Approach, 2014, International Journal of Bio-Science and Bio-Technology vol. 6, No. 2, pp. 83-90 (Year: 2014).*

* cited by examiner

*Primary Examiner* — Matthew L Hamilton
(74) *Attorney, Agent, or Firm* — Revolution IP, PLLC

(57) ABSTRACT

According to the pet healthcare service platform of the present invention, it is possible to predict the probability of developing a disease and recommend items for checkup to a pet owner based on historical (disease history/health history) data that has already been provided to pets of similar groups (breed/gender/age/disease history/dietary habits/living environment, etc, Pre-send symptom self-diagnosis items related to the pet's disease to the pet owner on a regular or irregular basis to prompt the pet owner to answer the questionnaire, thereby preventing the pet owner from inadvertently missing information related to the pet's symptoms.

3 Claims, 6 Drawing Sheets

PET HEALTH MANAGEMENT SERVICE PLATFORM BASED ON ARTIFICIAL INTELLIGENCE LEARNING

CROSS REFERENCE TO RELATED APPLICATION

The present application claims priority to Korean Patent Application No. 10-2024-0082362 filed on Jun. 25, 2024, the entire contents of which is incorporated herein for all purposes by this reference.

BACKGROUND OF THE INVENTION

Technical Field

The present invention relates to pet healthcare services, and more specifically to a technique for predicting likely diseases, changes in health status, etc. in pets as a tool for assisted diagnosis.

Background Art

With the recent increase in interest in pets, their place in the home is shifting toward the concept of family.

These pets, like humans, will inevitably become ill and require treatment throughout their lives, and will require intensive health care, including exercise, diet, and medication, both during the brief periods of illness and treatment and, in severe cases, throughout their lives.

However, most pet owners do not live with their pets 24 hours a day and spend much of the day away from their pets, making real-time monitoring and health management of their pets difficult.

Therefore, there is a growing need for research into technologies that can more efficiently manage the health of pets by improving dietary habits and increasing exercise based on continuous monitoring of pets to prevent obesity, proactively eliminate causes of disease, and provide optimal medical solutions to owners in the event of disease.

Related prior art includes Korean Patent Registration No. 10-2187344 (registered Nov. 30, 2020) and Korean Patent Publication No. 10-2023-0072540 (published May 25, 2023).

Technical Problem

The present invention aims to provide a pet healthcare service platform that can predict possible diseases and changes in health status of pets in advance based on artificial intelligence learning.

SUMMARY OF THE INVENTION

Technical Solution

According to one aspect of the present invention, a computer implemented method for predicting pet health executed by a pet health management service platform server, comprising: (a) obtaining, for a pet under management, animal attribute information of at least one of breed, sex, and age and health history information of at least one of disease history, examination history, and symptom history for said pet under management; (b) based on at least one of said animal attribute information and said health history information collected for said managed pet, establishing a pet comparison group comprising at least one other pet to be clustered with said managed pet from a pre-established pet database; and (c) predicting, using said health history information of at least one other pet in said pet comparison group, a change in a health condition that is likely to occur in said managed pet in the future.

Effect of Invention

The pet health management service platform according to an embodiment of the present invention has the effect of predicting the probability of developing a disease and recommending items that need to be checked to pet owners based on health history data that has already been previously used for pets in a similar group (breed/gender/age/disease history/examination history/symptom history, etc.

Furthermore, the pet healthcare service platform according to an embodiment of the present invention can prevent missing information due to inattention of the pet owner related to the symptoms occurring in the pet by pre-sending symptom self-diagnosis items related to the predicted disease of the pet to the pet owner on a regular or irregular basis to prompt the pet owner to answer the questionnaire.

DETAILED DESCRIPTION OF THE INVENTION

Figure 1:
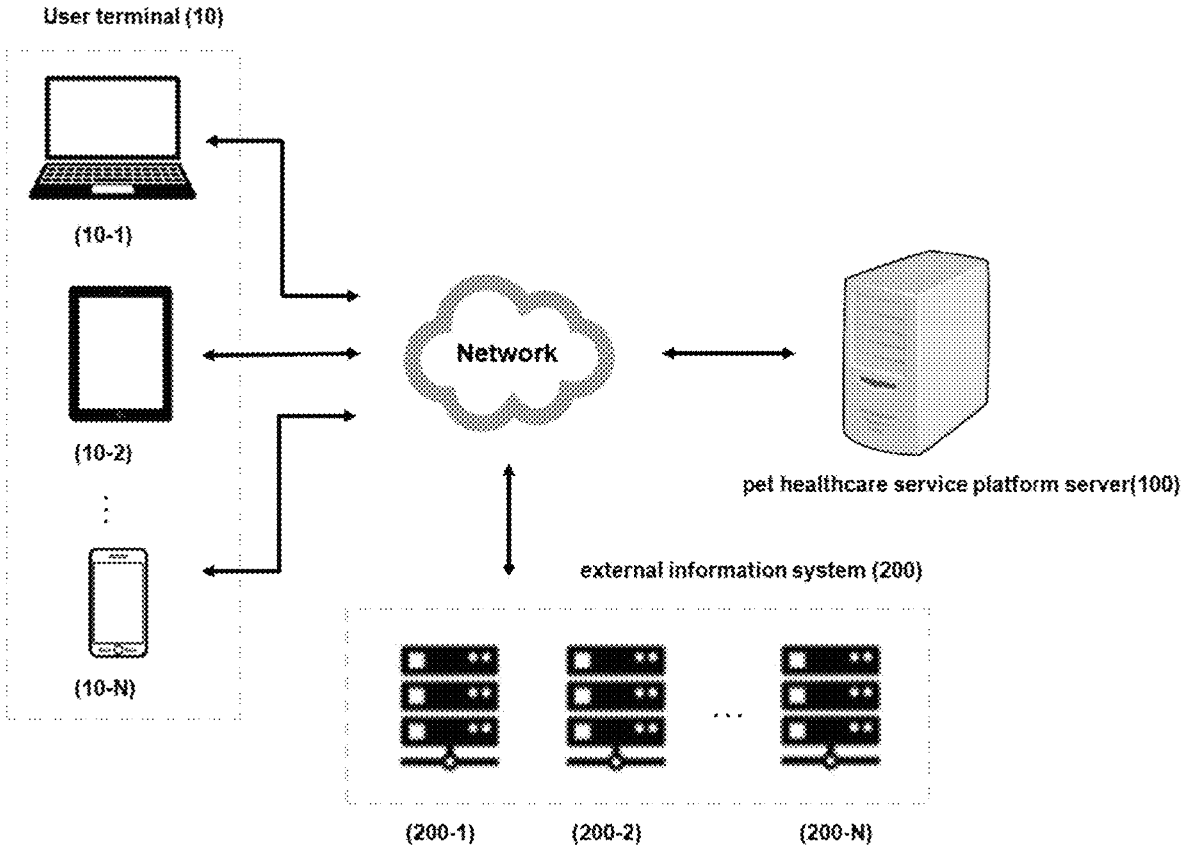
FIG. 1 is an overall system diagram of a pet healthcare service platform according to an embodiment of the present invention.

The present invention is subject to various modifications and can have many embodiments, certain of which are illustrated in the drawings and described in detail in the accompanying description. However, this is not intended to limit the invention to any particular embodiment and is to be understood to include all modifications, equivalents, or substitutions that fall within the scope of the present idea and technology.

In describing the present invention, detailed descriptions of related known art are omitted where it is believed that such descriptions would unnecessarily obscure the essence of the invention. In addition, numbers (e.g., first, second, etc.) used in the course of the description herein are merely identifiers to distinguish one component from another.

Also, throughout the specification, whenever a component is referred to as being “connected” or “coupled” to another component, it is to be understood that the component is or may be directly connected or coupled to the other component, but may also be connected or coupled through the intermediary of another component, unless the context specifically indicates to the contrary. Also, throughout the specification, whenever a part is said to “include” another component, it is meant to be inclusive of the other component, not exclusive of the other component, unless the context specifically indicates to the contrary. In addition, terms such as “part,” “module,” and the like used in the specification mean a unit that handles at least one function or operation, which may be implemented in one or more pieces of hardware or software or a combination of hardware and software.

Embodiments of the present invention will now be described in detail with reference to the accompanying drawings.

Figure 2:
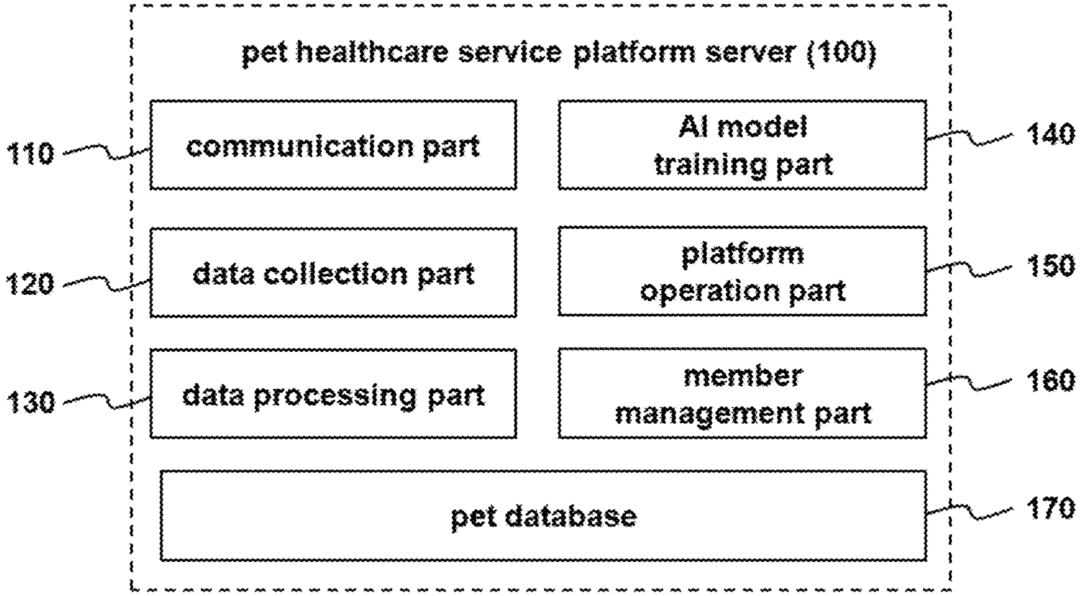
FIG. 2 is a simplified block diagram of a pet healthcare service platform server according to an embodiment of the present invention.

Explanation of FIG. 1 and FIG. 2

FIG. 1 is an overall system diagram of a pet healthcare service platform according to an embodiment of the present disclosure, and FIG. 2 is a simplified block diagram of a pet healthcare service platform server according to an embodiment of the present disclosure.

Referring to FIG. 1, a pet healthcare service platform server (hereinafter referred to as the platform server 100) according to an embodiment of the present invention may include a user terminal (see 10-1, 10-2, . . . 10-N of FIG. 1, hereinafter collectively referred to as figure mark 10) used by a user, such as a pet owner); an external information system (see 200-1, 200-2, . . . 200-N of FIG. 1, hereinafter collectively referred to as drawing designation 200) (e.g., veterinary hospital servers, veterinarian terminals, various pet-related service providers, animal-related laboratory servers, etc.

The platform server 100 may organize and manage the collected pet-related data into a database, and use the pet database to provide pet owners, veterinarians, and the like with diagnostic results, predictive results, and the like related to the health of the pet.

At this point, the platform server 100 may provide diagnostic results and predictive results related to the pet's health based on the artificial intelligence learning model.

To this end, the platform server 100 may be implemented including a communication part 110, a data collection part 120, a data processing part 130, an artificial intelligence model training part 140, a platform operation part 150, a member management part 160, a pet database 170, and the like, as shown in FIG. 2.

FIGS. 3 through 6 are flowcharts for illustrating a health change prediction method executed by a platform server in accordance with embodiments of the present disclosure.

A method for predicting pet health change, according to embodiments of the present invention, may comprise three steps: (a) obtaining information about the pet under management, (b) establishing a comparison group, and (c) predicting health change.

Hereinafter, with reference to FIGS. 3 through 6, a method for predicting changes in the health of a pet according to embodiments of the present invention will be described in detail.

Figure 3:
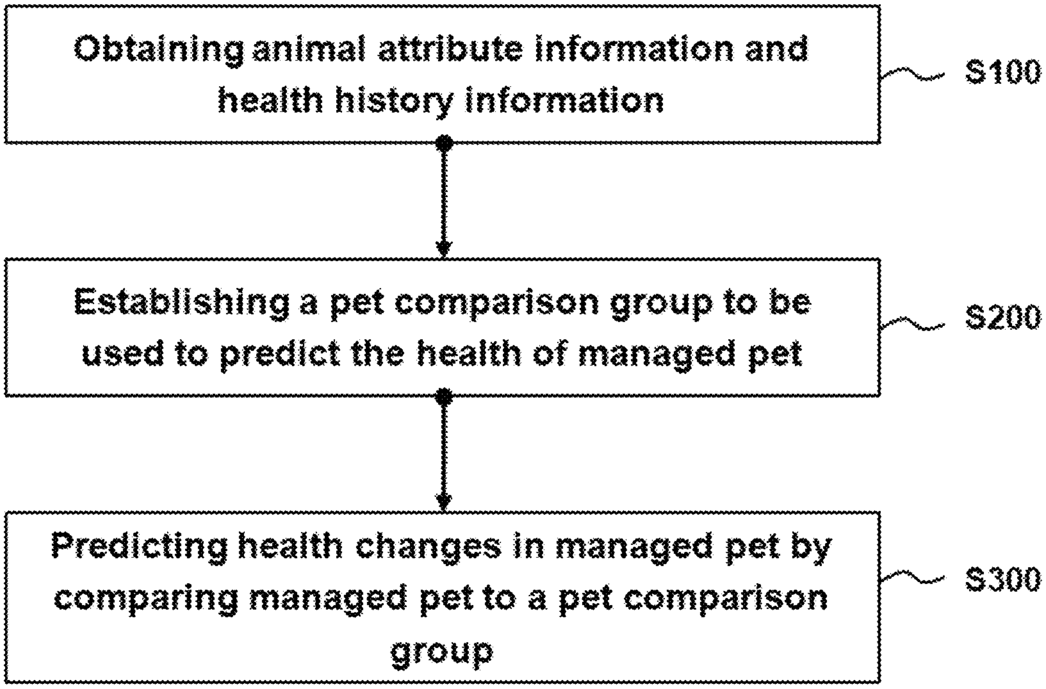
FIGS. 3 through 6 are flowcharts for illustrating a health change prediction method executed by a pet healthcare service platform server in accordance with embodiments of the present disclosure.

Step (a) in FIG. 3: Obtain Information about the Managed Pet

Referring to FIG. 3, a pet health change prediction method executed by the platform server 100 of the present disclosure includes obtaining, as pet information for a pet to be managed, animal attribute information of at least one of breed, sex, and age, and health history information of at least one of a history of illnesses that have occurred to date, a history of examinations, and a history of symptoms [see S100 in FIG. 3].

Here, the disease history may include treatment history for the disease that occurred.

Here, screening history may include test history, medical history, immunization history, etc.

In this context, symptom history means a history of symptoms recorded by the pet owner through the web or app related to the pet's health, in addition to the history objectively identified through medical practice, such as the disease history and examination history above.

Obtaining the information via step (a) above may be initiated, at the request of the pet owner, in accordance with a service subscribed to by the pet owner (e.g., a periodic health check service, etc.).

Step (b) in FIG. 3: Set Up the Comparison Group

Referring to FIG. 3, a method of predicting pet health changes executed by the platform server 100 of the present invention includes: establishing a pet comparison group comprising at least one other pet to be clustered with the subject pet from a pre-built pet database based on at least one of said animal attribute information and said health history information collected about the subject pet [see S200 in FIG. 3]; and establishing the subject pet and the pet comparison group from the pre-built pet database based on at least one of said animal attribute information and said health history information.

Here, the pet database may be a database in which the breed information, gender information, age information, disease history information, examination history information, symptom history information, and symptom history information described above are organized and recorded based on the name of an individual pet.

In this case, the pet database may record the disease history, examination history, and symptom history as individual items (i.e., individual disease items, individual examination items, and individual symptom items).

Depending on the system design model, the pet database may also include a pet activity history, a feeding history, a living environment history, and the like.

The pet database may also be recorded with time data for each individual history.

In the present invention, when performing an analysis on predicting health changes using an artificial intelligence learning model, it is not necessary to use all data sets in the pet database, but rather data sets in a comparison group selected by a special method.

The comparison groups and their datasets selected in the present invention may form a group of data that is more relevant to the animal attributes and/or health history of the pet being analyzed, thereby improving prediction accuracy compared to using all datasets in the pet database.

The method of selecting (setting) a comparison group will be described in detail below at S210, S220 of FIG. 4, S230, S240 of FIG. 5, and S250 of FIG. 6.

Step (c) in FIG. 3: Predict Health Changes

Referring to FIG. 3, a pet health change prediction method executed by the platform server 100 of the present disclosure includes: predicting a likely future change in a health condition of a pet under care, using said health history information of at least one other pet in said pet comparison group [see S300 in FIG. 3]; and predicting a likely future change in a health condition of said pet under care.

This will be discussed in more detail on S300 in FIG. 6 below.

Figure 4:
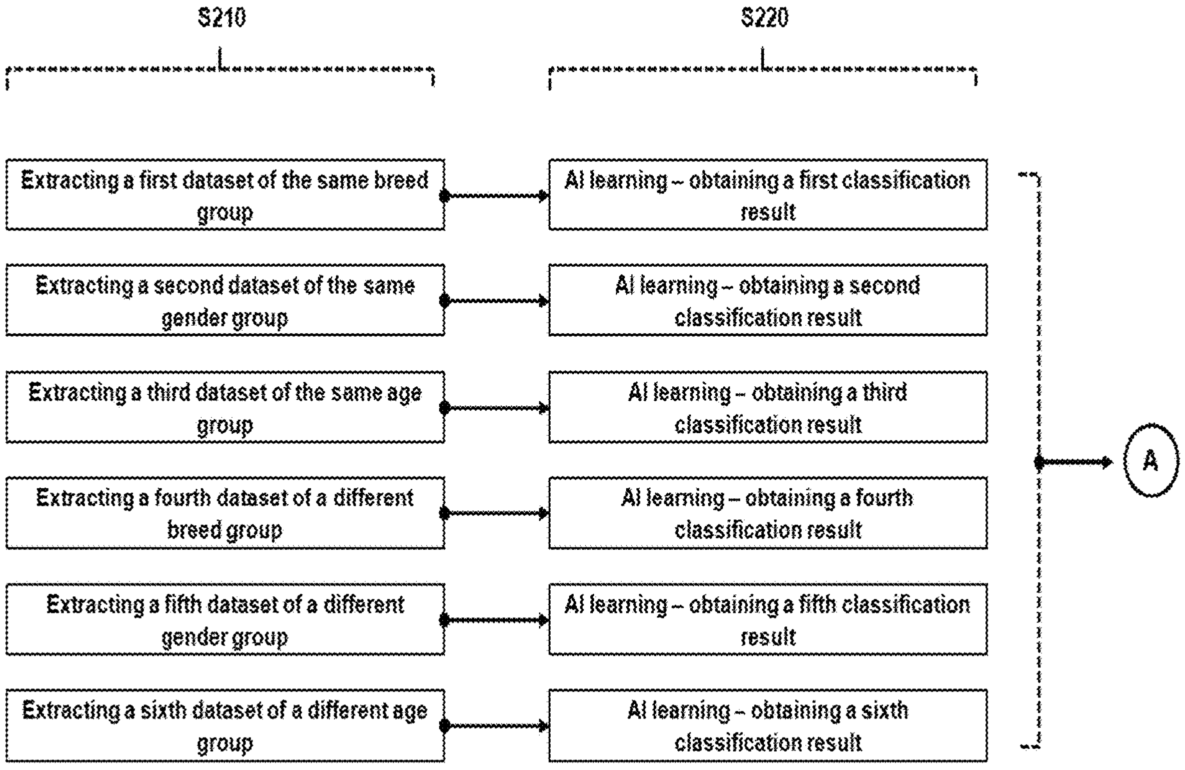

S210 in FIG. 4: Extracting a Preliminary Dataset

Figure 5:
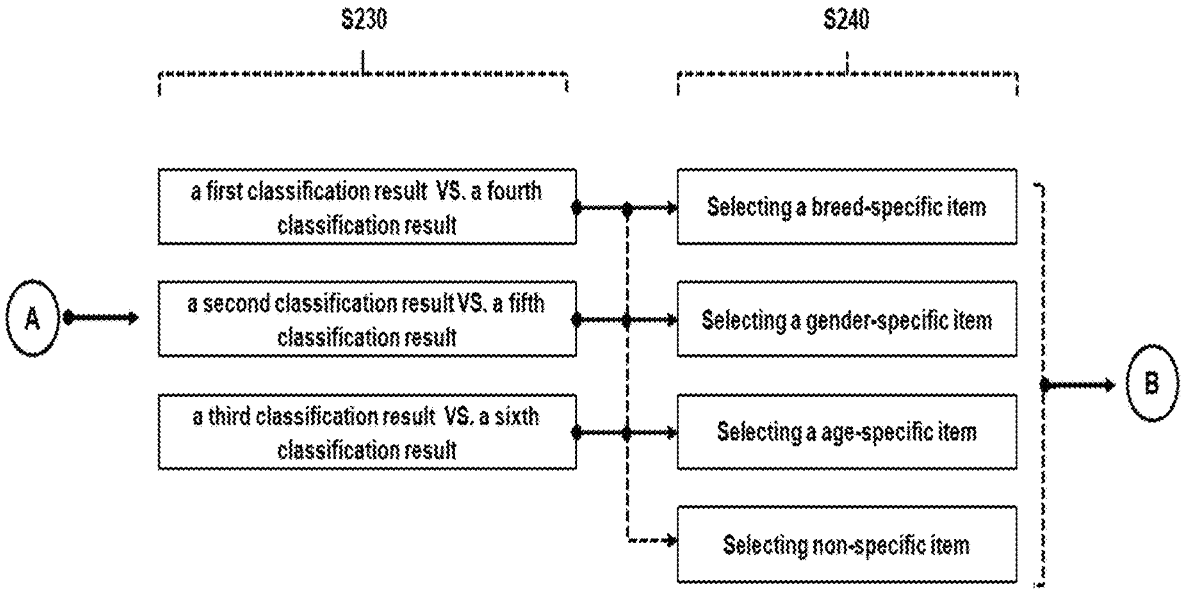

Referring to FIG. 4, the platform server 100 of the present disclosure extracts a preliminary dataset from S210 in FIG. 4 for selection of a suitable comparison group for predicting health changes through S300 in FIG. 5.

The preliminary dataset may include: 1) a first dataset of the same breed group, 2) a second dataset of the same gender group, 3) a third dataset of the same age group, 4) a fourth dataset of a different breed group, 5) a fifth dataset of a different gender group, and 6) a sixth dataset of a different age group, as shown at S210 in FIG. 4.

In this case, the first data set of the same breed group means, from said pet database, a data set of said disease history, said examination history, and said symptom history of each of said subject pet and other pets of the same breed in the same group.

In this case, the definition of same breed may vary depending on the design of the system model. For example, it may be possible to define an identical breed as only a breed that is a complete match to a specific breed, or it may be possible to define an identical breed as a similar breed that has a significant genetic link to a specific breed.

In this case, the second dataset of the same gender group is a dataset of said disease history, said examination history, and said symptom history of each of the other pets of the same gender group as the subject pet from said pet database.

In this case, the third dataset of the same age group is a dataset of the disease history, the examination history, and the symptom history of each of the other pets in the same age group as the subject pet from the pet database.

The definition of the same age may also depend on the design of the system model. For example, if it is desirable to group several ages according to the life cycle of a pet, even if they are not necessarily the same age, the entire age range can be defined as the same age.

In other words, the first through third data sets described above extract data of other pets that are related to the managed pet by animal attributes.

In contrast, the fourth through sixth datasets described below extract data from other pets that are not related to the managed pet by animal attributes.

In this case, the fourth data set of the different breed group means, from the pet database, a data set of the disease history, the examination history, and the symptom history of each of the other pets in the remaining group (hereinafter referred to as the exclusion group) that are not of the same breed as the subject pet.

In this case, the fifth data set of the other gender group means, from said pet database, a data set of said disease history, said examination history, and said symptom history of each of the other pets in the exclusion group that are not of the same gender as the subject pet.

In this case, the sixth dataset of the different age group means, from said pet database, a dataset of said disease history, said examination history, and said symptom history of each of the other pets in the exclusion group that are not in the same age group as the subject pet.

As described above, in extracting the preliminary dataset, the reason for extracting the same-group and excluded-group datasets separately is that In general, the accuracy and reliability of analysis results (classification results) using an AI learning model is affected by the quality of the input data itself, i.e., the better quality input data is selected, the more accurate and reliable the analysis results can be.

In this regard, it may be beneficial to use a dataset of a homogeneous group of pets that are similar in breed, gender, and age to the pet you are trying to predict.

However, it remains to be validated in practice that a homogeneous dataset of similar breed, gender, and age to the pet under management is a qualitatively superior dataset that can increase the accuracy and reliability of health change predictions.

Therefore, in the present invention, by comparing the prediction results when a homogeneous group dataset is input with the prediction results when an excluded group dataset is input, it is possible to determine whether an effective homogeneous group dataset actually exists and, if so, to use the effective dataset with high weight. This will be clearly understood with reference to S220 of FIGS. 4 and S230 and S240 of FIG. 5.

S220 in FIG. 4: Obtaining Preliminary Results According to the AI Learning Model Referring to FIG. 4, the platform server 100 of the present disclosure obtains the results of an artificial intelligence learning model given the preliminary data set described above as input.

In the present invention, the artificial intelligence learning model used at S220 of FIG. 4 may vary, and any one of commercially available artificial intelligence learning models may be used, or a combination of a plurality of models may be used, and is of course not limited to any particular algorithmic artificial intelligence model.

In this case, the artificial intelligence learning model may be a model that has been pre-trained on all of the datasets in the pet database.

Accordingly, at S220 of FIG. 4, each of the first data set to the sixth data set is input to the pre-trained artificial intelligence learning model for pets, and a classification result according to each data set is obtained.

More specifically, at S220 of FIG. 4, (1) the first dataset may be input to a pre-trained artificial intelligence learning model for pets to obtain a first classification result that quantifies and classifies 1) the correlation of disease items by breed, 2) the correlation of examination items by breed, and 3) the correlation of symptom items by breed, respectively.

Further, at S220 of FIG. 4, (2) the second dataset may be input to the artificial intelligence learning model for pets to obtain a second classification result that quantifies and classifies 1) a correlation by disease item by gender, 2) a correlation by examination item by gender, and 3) a correlation by symptom item by gender, respectively.

Further, at S220 of FIG. 4, (3) the third dataset is input to the artificial intelligence learning model for pets to obtain a third classification result that quantifies and classifies 1) the correlation of disease items by age, 2) the correlation of examination items by age, and 3) the correlation of symptom items by age, respectively.

Further, at S220 of FIG. 4, (4) the above fourth dataset is input to the above artificial intelligence learning model for pets to obtain a fourth classification result that quantifies and classifies 1) the correlation of disease items by different breeds, 2) the correlation of examination items by different breeds, and 2) the correlation of symptom items by different breeds, respectively.

Further, at S220 of FIG. 4, (5) the above fifth dataset is input to the above artificial intelligence learning model for pets to obtain a fifth classification result that quantifies and classifies 1) the correlation of disease items by different genders, 2) the correlation of examination items by different genders, and 2) the correlation of symptom items by different genders, respectively.

Further, at S220 of FIG. 4, the sixth dataset is input to the above artificial intelligence learning model for pets to obtain a sixth classification result that quantifies and classifies 1) the correlation of disease items according to different ages, 2) the correlation of examination items according to different ages, and 3) the correlation of symptom items according to different ages, respectively.

S230 & S240 in FIG. 5: Comparison of Preliminary Results and Selection of Specializations Referring to FIG. 5, the platform server 100 of the present disclosure compares the results of the artificial intelligence learning model when the preliminary data set described above is input.

The platform server 100 of the present invention compares, with respect to a variety, between said first classification result based on input of a first dataset of a homogeneous group and said fourth classification result based on input of a fourth dataset of an excluded group, for the same individual item.

That is, comparing the classification values for A-1 diseases in the same group to the classification values for A-1 diseases in the excluded group, comparing the classification values for A-2 diseases in the same group to the classification values for A-2 diseases in the excluded group, and comparing the classification values for B-1 symptoms in the same group to the classification values for B-1 symptoms in the excluded group.

Accordingly, if there exists a dominant item whose itemized value according to the first classification result is higher than the itemized value according to the fourth classification result by more than a predetermined threshold, the platform server 100 of the present invention may extract the dominant item, and select the extracted dominant item as a breed-specific item that maps to one of 1) a breed-specific disease item, 2) a breed-specific screening item, and 3) a breed-specific symptom item according to the item classification.

Similar to the above method, the platform server 100 of the present invention compares, with respect to gender, the second classification result based on the input of the second dataset of the same group and the fifth classification result based on the input of the fifth dataset of the excluded group, for the same individual items.

Accordingly, if there exists a dominant item whose itemized value according to the second classification result is higher than the itemized value according to the fifth classification result by more than a predetermined threshold, the platform server 100 of the present invention may extract the dominant item, and select the extracted dominant item as a gender-specific item that maps to one of 1) a gender-specific disease item, 2) a gender-specific screening item, and 3) a gender-specific symptom item according to the item classification.

Similar to the above method, the platform server 100 of the present invention compares, with respect to age, the results of said third classification based on the input of the third dataset of the same group and the results of said sixth classification based on the sixth dataset of the excluded group for the same individual items.

Accordingly, if there exists a dominant item whose itemized value according to the third classification result is higher than the itemized value according to the sixth classification result by a predetermined threshold, the platform server 100 of the present invention may extract the dominant item, and select the extracted dominant item as an age-specific item that maps to one of 1) an age-specific disease item, 2) an age-specific screening item, and 3) an age-specific symptom item according to the item classification.

Using the methods described above, first, homogeneous group-specific items (i.e., disease items, test items, symptom items) that are low-correlated in the excluded group but high-correlated in the homogeneous group can be distinguished.

Second, it can also be observed that for items that are highly correlated in the same group but also highly correlated in the excluded group, using only the same group dataset is not particularly helpful in improving the accuracy and reliability of the outcome prediction. In these cases, expanding the dataset, if possible, may be more helpful in improving the accuracy and reliability of outcome predictions.

From this perspective, for disease items, screening items, and symptom items that do not correspond to the above breed-specific items, the above gender-specific items, or the above age-specific items, the platform server 100 of the present invention may classify them as non-specific items that are not related to animal attribute information.

Figure 6:
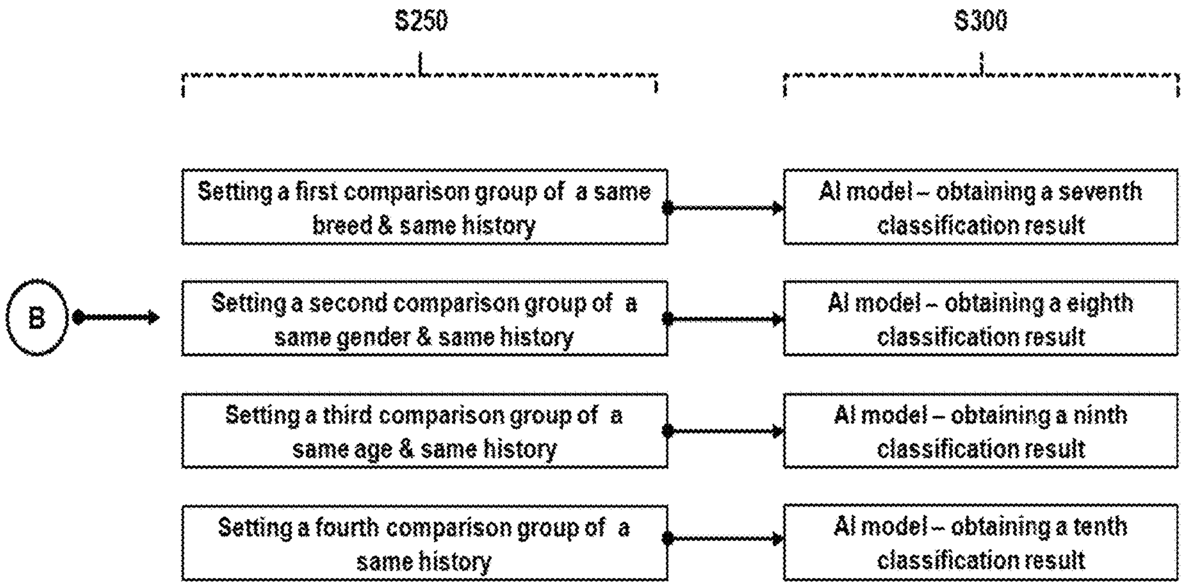

S250 in FIG. 6: Setup of the Comparison Group

Referring to FIG. 6, the platform server 100 of the present invention may set comparison groups according to said breed-specific items, said gender-specific items, said age-specific items, and said non-specific items as follows.

The platform server 100 of the present invention may extract, from the pet database, other pets that are of the same breed as the pet under management and that include a history of the same items as the breed-specific items from the disease history, examination history, and symptom history of the pet under management, if the breed-specific items exist, and set the extracted breed-specific history other pets as the first pet comparison group.

Furthermore, the platform server 100 of the present invention may extract from the pet database another pet that is of the same gender as the pet under management and that includes a history of the same items as the gender-specific items from the disease history, examination history, and symptom history of the pet under management, if the gender-specific items exist, and set the extracted same-gender, same-history pet as a second pet comparison group.

In addition, the platform server 100 of the present invention may, if the age-specific item exists in the disease history, examination history, and symptom history of the managed pet, extract from the pet database another pet that is the same age as the managed pet and includes a history for the same item as the age-specific item, and set the extracted same-age, same-history other pet as a third pet comparison group.

Furthermore, the platform server 100 of the present invention may, if there is a non-specific item classified as not corresponding to said breed-specific item, said gender-specific item, or said age-specific item in the disease history, examination history, or symptom history of said managed pet, extract other pets having a history of said non-specific item from said pet database, and set the extracted other pets with the same history as said non-specific item as a fourth pet comparison group.

Thus, according to the present invention, the accuracy and reliability of the prediction results can be improved by utilizing a more effective data set through the process of establishing a comparison group utilizing preliminary results using an artificial intelligence learning model.

S6 in FIG. 300: Predicting Health Changes

The platform server (100) of the present invention selects at least one dataset of said first pet comparison group, said second pet comparison group, said third pet comparison group, and said fourth pet comparison group, and inputs said dataset of health history information into an artificial intelligence learning model for pets to predict changes in health conditions that are likely to occur in the future in said managed pet.

More specifically, the platform server 100 of the present invention may input the dataset of health history information of the first pet comparison group into the artificial intelligence learning model for pets to obtain a seventh classification result that quantifies the correlation with other disease items, other examination items, and other symptom items, respectively, based on said breed-specific items, if there are items corresponding to said breed-specific items in said health history of said managed pet.

For example, if a B-1 symptom recorded in the symptom history of a managed pet falls under a breed-specific symptom category, and the AI analysis predicts that the B-1 symptom is highly correlated with A-1 disease using only a dataset of other pets of the same breed with B-1 symptoms, this means that the managed pet is likely to develop A-1 disease in the future.

From a similar perspective to the above, the platform server 100 of the present invention may input the dataset of health history information of the second pet comparison group into the artificial intelligence learning model for pets to obtain an eighth classification result that quantifies the correlation with other disease items, other examination items, and other symptom items, respectively, based on said gender-specific items, if there are items corresponding to said gender-specific items in said health history of said managed pet.

From a similar perspective to the above, the platform server 100 of the present invention may input the dataset of health history information of the third pet comparison group into the artificial intelligence learning model for pets to obtain a ninth classification result that quantifies the correlation with other disease items, other examination items, and other symptom items, respectively, based on said age-specific items, if there are items corresponding to said age-specific items in said health history of said managed pet.

In a similar perspective to the above, the platform server 100 of the present invention may input the dataset of health history information of the fourth pet comparison group into the artificial intelligence learning model for pets, if there are items corresponding to said non-specific items in said health history of said managed pet, and obtain a tenth classification result that quantifies the correlation with other disease items, other examination items, and other symptom items, respectively, based on said non-specific items.

Accordingly, the platform server 100 of the present invention may extract correlation information having a correlation above a predetermined threshold, or having a correlation above a predetermined grade according to a numerical grading, from each of the classification results using the seventh classification result, the eighth classification result, the ninth classification result, and the tenth classification result.

In this case, the correlation information may include, for each item of the disease history, examination history, and symptom history that occurred in the subject pet, 1) a disease item-disease item-symptom item correlation based on the disease item that occurred, 2) an examination item-disease item-symptom item correlation based on the examination item that occurred, and 3) a symptom item-disease item-examination item correlation based on the symptom item that occurred.

Accordingly, the platform server 100 of the present invention may, using the above-extracted correlation information, output information (such as screen guidance) to the caretaker regarding disease items, test items, symptom items that are likely to be associated in the future for each item of the above health history that has occurred in the managed pet.

At this time, the platform server 100 of the present invention may output correlation information according to the seventh classification result to the tenth classification result, respectively, or may output a composite score of these classification results. In addition, the platform server 100 of the present invention may assign predetermined weights to each of the breed-specific items, gender-specific items, age-specific items, and non-specific items in the process of comprehensively scoring the seventh classification result to the tenth classification result.

According to the present invention, by providing information (e.g., periodic information) to a pet owner in advance about other diseases that are likely to occur in the future, other symptoms, necessary checkup items, etc. in relation to the pet's previous disease history, checkup history, and symptom history, it is possible to help prevent such diseases and solve problems such as missed symptoms and missed checkup items due to neglect of care.

Although the above has been described with reference to embodiments of the present invention, it will be readily understood by one having ordinary skill in the art that various modifications and changes can be made to the present invention without departing from the ideas and scope of the invention described in the following patent claims.

The invention claimed is:

1. A computer implemented method for predicting pet health executed by a pet healthcare service platform server, the method comprising:

(a) obtaining, by the pet healthcare service platform server, pet information about a managed pet, comprising animal attribute information of at least one of breed, sex, and age, and health history information of at least one of disease history, examination history, and symptom history from a user device associated with an owner of the managed pet;

(b) establishing, by the pet healthcare service platform server, based on at least one of the animal attribute information and the health history information collected about the managed pet, a pet comparison group comprising at least one other pet from a pre-built pet database to which the managed pet is to be clustered and compared, wherein the step (b) comprises:

extracting, by the pet healthcare service platform server, from the pet database, a first dataset of the disease history, the examination history, and the symptom history for each of other pets of a same-breed group as the managed pet;

extracting, by the pet healthcare service platform server, from the pet database, a second dataset of the disease history, the examination history, and the symptom history for each of other pets of a same-gender group as the managed pet;

extracting, by the pet healthcare service platform server, from the pet database, a third dataset of the disease history, the examination history, and the symptom history of each of other pets in a same-age group as the managed pet;

extracting, by the pet healthcare service platform server, from the pet database, a fourth dataset of the disease history, the examination history, and the symptom history for each of other pets in a different-breed group that are not of the same breed as the managed pet;

extracting, by the pet healthcare service platform server, from the pet database, a fifth dataset of the disease history, the examination history, and the symptom history for each of other pets in a different-gender group that are not of the same gender as the managed pet;

extracting, by the pet healthcare service platform server, from the pet database, a sixth dataset of the disease history, the examination history, and the symptom history for each of other pets in a different-age group that are not of the same age as the managed pet;

inputting, by the pet healthcare service platform server, the first dataset into a pre-trained artificial intelligence learning model for pets;

obtaining a first classification result that quantifies a correlation of disease items by breed, a correlation of examination items by breed, and a correlation of symptom items by breed, respectively;

inputting, by the pet healthcare service platform server, the second dataset into the artificial intelligence learning model for pets;

obtaining a second classification result that quantifies a correlation of disease items by gender, a correlation of examination items by gender, and a correlation of symptom items by gender, respectively;

inputting, by the pet healthcare service platform server, the third dataset into the artificial intelligence learning model for pets;

obtaining a third classification result that quantifies a correlation of disease items by age, a correlation of examination items by age, and a correlation of symptom items by age, respectively, inputting, by the pet healthcare service platform server, the fourth dataset into the artificial intelligence learning model for pets;

obtaining a fourth classification result that quantifies a correlation of disease items by different breeds, a correlation of examination items by different breeds, and a correlation of symptom items by different breeds, respectively;

inputting, by the pet healthcare service platform server, the fifth dataset into the artificial intelligence learning model for pets;

obtaining a fifth classification result that quantifies a correlation of disease items by different genders, a correlation of examination items by different genders, and a correlation of symptom items by different genders, respectively;

inputting, by the pet healthcare service platform server, the sixth dataset into the artificial intelligence learning model for pets;

obtaining a sixth classification result that quantifies a correlation of disease items by different ages, a correlation of examination items by different ages, and a correlation of symptom items by different ages, respectively, comparing, by the pet healthcare service platform server, the first classification result and the fourth classification result for individual item by:

determining a dominant item exists when an itemized value according to the first classification result is higher than an itemized value according to the fourth classification result by a predetermined threshold, extracting the dominant item, and selecting the extracted dominant item as a breed-specific item that maps to one of a breed-specific disease item, a breed-specific examination item, and a breed-specific symptom item based on an item classification;

comparing, by the pet healthcare service platform server, the second classification result and the fifth classification result for individual item by:

determining a dominant item exists when in which an itemized value according to the second classification result is higher than an itemized value according to the fifth classification result by a predetermined threshold, extracting the dominant item, and selecting the extracted dominant item as a gender-specific item that maps to one of a gender-specific disease item, a gender-specific examination item, and a gender-specific symptom item based on an item classification;

comparing, by the pet healthcare service platform server, the third classification result and the sixth classification result for individual item by:

determining a dominant item in which an itemized value according to the third classification result is higher than an itemized value according to the sixth classification result by more than a predetermined threshold, extracting the dominant item, and selecting the extracted dominant item as an age-specific item that maps to one of an age-specific disease item, an age-specific examination item, and an age-specific symptom item based on the item classification;

classifying, by the pet healthcare service platform server, for disease items, examination items, and symptom items that do not correspond to the breed-specific items, the gender-specific items, and the age-specific items, them as non-specific items that are not related to animal attribute information;

extracting, by the pet healthcare service platform server, from the pet database, other pets that are of the same breed as the managed pet and include a history for the breed-specific item when the breed specific item exists in the disease history, the examination history or the symptom history of the managed pet;

setting, by the pet healthcare server platform server, the extracted other pets having the same breed and the history of the breed-specific item as a first pet comparison group;

extracting, by the pet healthcare service platform server, from the pet database, other pets that are of the same gender as the managed pet and include a history for the gender-specific item when the gender-specific item exists in the disease history, the examination history, or the symptom history of the managed pet;

setting, by the pet healthcare server platform server, the extracted other pets having the same gender and the history of the gender-specific item as a second pet comparison group;

extracting, by the pet healthcare service platform server, from the pet database, other pets that are of the same age as the managed pet and include a history for the age-specific item when the age specific item exists in the disease history, the examination history, or the symptom history of the managed pet;

setting, by the pet healthcare server platform server, the extracted other pets having the same age and the history of the age-specific item as a third pet comparison group;

extracting, by the pet healthcare service platform server, from the pet database, other pets that include a history for the non-specific item when the non-specific item exists in the disease history, the examination history, or the symptom history of the managed pet;

setting the extracted other pets having the history of the non-specific item as a fourth pet comparison group;

(c) predicting, by the pet healthcare service platform server, using the health history information of at least one other pet in said pet comparison group, a change in a health condition that is likely to occur in the managed pet in a future, wherein the step (c) comprises:

selecting, by the pet healthcare service platform server, a dataset of each of the first pet comparison group, the second pet comparison group, the third pet comparison group, and the fourth pet comparison group, and inputting the dataset of health history information into the artificial intelligence learning model for pets to predict a change in a health condition likely to occur in the managed pet in the future; and (d) transmitting, by the pet healthcare service platform server, the predicted change in the health condition to the user device associated with the owner of the managed pet, wherein the predicted change in the health condition refers to probability of the managed pet developing one or more diseases and a recommendation of items to be checked by the owner of the managed pet based on health history data.

2. The method of claim 1, wherein the step (c) further comprises:

inputting, by the pet healthcare service platform server, a dataset of health history information of the first pet comparison group into the artificial intelligence learning model for pets when an item corresponding to the breed-specific item exists in the health history of the managed pet;

obtaining a seventh classification result that quantifies a correlation with other disease items, other examination items, and other symptom items, respectively, based on the breed-specific item;

inputting, by the pet healthcare service platform server, a dataset of health history information of the second pet comparison group into the artificial intelligence learning model for pets when an item corresponding to the gender-specific item exists in the health history of the managed pet;

obtaining an eighth classification result that quantifies a correlation with other disease items, other examination items, and other symptom items, respectively, based on the gender-specific item;

inputting, by the pet healthcare service platform server, a dataset of health history information of the third pet comparison group into the artificial intelligence learning model for pets when an item corresponding to the age-specific item exists in the health history of the managed pet;

obtaining a ninth classification result that quantifies a correlation with other disease items, other examination items, and other symptom items, respectively, based on the age-specific item;

inputting, by the pet healthcare service platform server, a dataset of health history information of the fourth pet comparison group into the artificial intelligence learning model for pets when an item corresponding to the non-specific item exists in the health history of the managed pet; and obtaining a tenth classification result that quantifies a correlation with other disease items, other examination items, and other symptom items, respectively, based on the non-specific item.

3. The method of claim 2, wherein the step (c) further comprises:

extracting, by the pet healthcare service platform server, correlation information from each of the seventh classification result, the eighth classification result, the ninth classification result, and the tenth classification result, the extracted correlation information having a correlation equal to or greater than a predetermined threshold or having a predetermined rating equal to or higher than a predetermined grade based on numerical grading; and outputting, by the pet healthcare service platform server, using the extracted correlation information, information regarding disease items, examination items, and symptom items that are likely to be associated with each of the health history items that have occurred in the managed pet in the future, wherein the correlation information includes, for each item of a disease history, an examination history, and a symptom history that has occurred in the managed pet, correlations among disease items, examination items, and symptom items, including:

correlations among a disease item, an examination item, and a symptom item based on a disease item that has occurred;

correlations among an examination item, a disease item, and a symptom item based on an examination item that has occurred; and correlations among a symptom item, a disease item, and an examination item based on a symptom item that has occurred.

* * * * *